US011567065B2

(12) United States Patent
Sykulev et al.

(10) Patent No.: US 11,567,065 B2
(45) Date of Patent: *Jan. 31, 2023

(54) MEASURING FREQUENCY OF PATHOGEN-SPECIFIC T CELLS IN PERIPHERAL BLOOD

(71) Applicant: THOMAS JEFFERSON UNIVERSITY, Philadelphia, PA (US)

(72) Inventors: Yuri Sykulev, Newtown Square, PA (US); Nadezhda Anikeyeva, Bryn Mawr, PA (US); Neal Flomenberg, Philadelphia, PA (US); Dolores Grosso, Philadelphia, PA (US)

(73) Assignee: Thomas Jefferson University, Philadelphia, PA (US)

( * ) Notice: Subject to any disclaimer, the term of this patent is extended or adjusted under 35 U.S.C. 154(b) by 684 days.

This patent is subject to a terminal disclaimer.

(21) Appl. No.: 15/738,498

(22) PCT Filed: Jun. 24, 2016

(86) PCT No.: PCT/US2016/039313
§ 371 (c)(1),
(2) Date: Dec. 20, 2017

(87) PCT Pub. No.: WO2016/210297
PCT Pub. Date: Dec. 29, 2016

(65) Prior Publication Data
US 2018/0180593 A1    Jun. 28, 2018

Related U.S. Application Data

(60) Provisional application No. 62/183,997, filed on Jun. 24, 2015.

(51) Int. Cl.
| | | |
|---|---|---|
| *G01N 33/53* | (2006.01) | |
| *G01N 33/50* | (2006.01) | |
| *G01N 33/58* | (2006.01) | |
| *C12N 5/0783* | (2010.01) | |
| *G01N 33/552* | (2006.01) | |

(52) U.S. Cl.
CPC .......... *G01N 33/505* (2013.01); *C12N 5/0636* (2013.01); *C12N 5/0638* (2013.01); *G01N 33/552* (2013.01); *G01N 33/582* (2013.01); *G01N 2610/00* (2013.01); *G01N 2800/52* (2013.01)

(58) Field of Classification Search
CPC .. G01N 33/505; G01N 33/552; G01N 33/582; G01N 2610/00; G01N 2800/52; C12N 5/0638; C12N 5/0636
See application file for complete search history.

(56) References Cited

U.S. PATENT DOCUMENTS

| | | |
|---|---|---|
| 2004/0058399 A1 | 3/2004 | Lalvani |
| 2007/0059845 A1 | 3/2007 | Moritz et al. |
| 2012/0276557 A1 | 11/2012 | Scheffold et al. |
| 2013/0288229 A1 | 10/2013 | Deml et al. |
| 2014/0120557 A1 | 5/2014 | Xie et al. |
| 2015/0030533 A1 | 1/2015 | Algate et al. |

FOREIGN PATENT DOCUMENTS

WO    2015017889 A1    2/2015

OTHER PUBLICATIONS

Su et al.( J Immunol 1993; 151:658-667).*
Diener et al. (Acta Biomaterialia 8 (2012).*
Seurynck-Servoss et al.(Anal Biochem. Dec. 1, 2007; 371(1): 105-115).*
Cox et al (JALA, 2004;pp. 16-23).*
Corada et al., Blood, 2001; 97:1679-84.*
E. A. Padlan, Adv Prot Chem 49:57-133; 1996.*
Fooksman et al Annu. Rev. Immunol. 2010. 28:79-105.*
(Davignon et al; 1981;Jimmunol 127:590-595).*
Huse et al. "Spatial and temporal dynamics of T cell receptor signaling with a photoactivatable agonist", Immunity, Jul. 12, 2007 (Jul. 12, 2001), vol. 27, pp. 76-88.
Beal et al. "Kinetics of early T cell receptor signaling regulate the pathway of lytic granule delivery to the secretory domain," Immunity, Oct. 16, 2009 (Oct. 16, 2009), vol. 31, pp. 632-642.
Altman, J.D., et al., "Phenotypic Analysis of Antigen-Specific T Lympohcytes", Science, vol. 274, No. 5284, pp. 94-96, 1996.
International Search Report and Written Opinion dated Sep. 26, 2016 in International Application No. PCT/US2016/039313.

* cited by examiner

*Primary Examiner* — Carmencita M Belei
(74) *Attorney, Agent, or Firm* — Riverside Law, LLP

(57) ABSTRACT

A method for detecting and quantifying of the frequency of T cells to multiple antigenic peptide epitopes comprising: measuring intracellular Ca2+ signaling in individual T cells that are labeled with Ca2+ sensitive fluorophore; wherein said T cells are placed on the glass bottom of a well-covered with antibodies or other capturing proteins specific for non-stimulatory T cells' surface receptors and wherein a peptide antigens are injected into the well and the peptide binds to MHC molecules on the T-cell surface, wherein an increase in the intracellular concentration of Ca2+ in responding T cells leads to rise in intracellular fluorescence that is detected by fluorescent microscope and wherein the response rate of said detected fluorescence can be utilized to determine the quantity of responding T cells and the efficiency of said cells.

3 Claims, 13 Drawing Sheets

Specification includes a Sequence Listing.

2 out of 57 cells are unresponsive

MEASURING FREQUENCY OF PATHOGEN-SPECIFIC T CELLS IN PERIPHERAL BLOOD

CROSS REFERENCE TO RELATED APPLICATIONS

This application is a National Phase under 35 U.S.C. 371 of International Application No. PCT/US16/39313, filed Jun. 24, 2016, which claims the benefit of U.S. Provisional Application Ser. No. 62/183,997, filed Jun. 24, 2015, which are hereby incorporated by reference in their entirety.

REFERENCE TO A "SEQUENCE LISTING," A TABLE, OR A COMPUTER PROGRAM LISTING APPENDIX SUBMITTED AS AN ASCII TEXT FILE

The present application hereby incorporates by reference the entire contents of the text file named "205961-0043-00US Sequence Listing.txt" in ASCII format. The text file containing the Sequence Listing of the present application was created on Mar. 16, 2021 and is 829 bytes in size.

FIELD OF INVENTION

The present application is generally related to methods for evaluating the frequency of pathogen-specific and tumor-specific T cells and the kinetics of their response, reflecting the effectiveness of immune responses.

BACKGROUND OF THE INVENTION

Currently, determining the frequency of T cells with specificity of interest is performed by staining of the T cells with the pMHC/tetramers or intracellular staining for cytokine or ELISpot assays. While these processes have some ability to determine specificity of T-cells, each has significant limitations. Staining with the tetramers does not allow determining functional capacity of virus-specific T cells. ELISpot assay and intracellular cytokine staining provide information about functional activity of T cells, but does not detect antigen-specific cells that are unable to produce the indicator cytokine. In addition, ELISpot assay takes at least 24 hrs to complete, a time during which T cells are exposed to stimulation resulting in activation of initially antigen-inexperienced T cells contributing to potentially pseudo positive data.

Several United States patents or publications, or other literature have proposed mechanisms to determine frequency of T-cells with specificity. However, these mechanisms are generally lacking in one or more features and do not utilize the specificity mechanism of the embodiments disclosed herein. US Pub. No. 2015/0030533—entitled "Compositions and methods for the detection diagnosis and therapy of hematological malignancies" proposes methods for eliciting immune and T cell responses to specific malignancy-related antigenic polypeptides. The '533 Publication, however, does not address quantifying the frequency of T cells through measurement of intracellular $Ca^{2+}$ in individual T Cells as in a new method defined herein.

US Pub. No 2007/0059845—entitled "Reagents for the detection of protein phosphorylation in T-cell receptor signaling pathways" is related to phosphorylation sites downstream of the T-cell receptor that provides for selective detection and quantification of phosphorylated proteins. However, there is no mention of detection strategies incorporating measurements of $Ca^{2+}$ in individual T cells as in the new methods described herein.

Altman, Moss, Goulder, et al.: "Phenotypic Analysis of Antigen-Specific T Lymphocytes"; Science 274 (5284): 94-96; addresses a tetramer assay to detect and quantify T-Cells that are specific for a given antigen within a blood sample. However, the Altman publication does not detect via $Ca^{2+}$ in individual T cells as in the methods disclosed herein.

Indeed, US Pub. Nos. '533 and '845, appear to generally describe the field regarding detection of T-cells and related signaling pathways. However, neither the '533 nor the '845 Publication provided any disclosure of measurement of calcium ions as a mechanism for identifying specific or individual T cells and thus fail to provide mechanisms for detection and quantification of virus specific T-cells.

The Altman publication is related to Tetramer technology, which is described in this disclosure. However, the Tetramer technology does not measure $Ca^{2+}$ signaling, and instead measures TCR specificity. Accordingly, this assay utilizes a completely different detection strategy.

Therefore, there is a need for new methods and strategies for detecting and quantifying virus specific T Cells. Through this new methodology, we can better determine the frequency of T cells that will reveal a much better correlation with clinical outcomes and will provide information regarding efficacy of T-cell responses.

SUMMARY OF THE INVENTION

In accordance with these and other objects, a first embodiment of an invention disclosed herein is directed to a method of measuring the frequency of T cells specific for multiple peptide epitopes as well as efficiency of the T-cell responses.

Further embodiments are related to an assay for detecting and quantification of the frequency of T cells to multiple antigenic peptide epitopes. The Assay measures intracellular $Ca^{2+}$ signaling in individual T cells. T cells are labeled with $Ca^{2+}$ sensitive fluorophore and are placed on the glass bottom of a well covered with antibodies against non-stimulatory T cells' surface receptors. A peptide antigen is injected into the well and the peptide binds to MHC molecules on the T-cell surface. Increase in the intracellular concentration of $Ca^{2+}$ in responding T cells leads to rise in cell fluorescence that is detected by fluorescent microscope.

A method for detection of the frequency of T cells responding to multiple antigenic peptide epitopes comprising: coating glass surface with an agent capable to bind either an antibody or other capturing proteins; covering the surface with an antibody or capturing proteins that binds to a receptor on T-cell surface without interfering with $Ca^{2+}$ flux; adding cloned or polyclonal T cells or gamma/delta T cells labeled with $Ca^{2+}$ sensitive fluorophore to the surface to generate monolayer of the T cells; taking first image of the T-cell monolayer to determine a level of background fluorescence in every individual cell; adding a single or multiple peptide epitopes or live target cells presenting potential peptide epitopes to the T-cell monolayer; measuring the level of fluorescence in every individual T cells on the monolayer by taking second image of the T-cell monolayer followed by peptide(s) or live target cells addition bearing peptide epitope; quantifying responses of individual T cells by subtracting intracellular fluorescence measured after taking the first image from that acquired after the second image.

A method for measuring kinetics of $Ca^{2+}$ flux in T cells that form monolayer on the glass surface in response to antigenic peptides or live target cells comprising: immobilizing T cells labeled with $Ca^{2+}$ sensitive fluorophore on the glass bottom of a well, covered with capturing antibody or a capturing protein that bind to non-stimulatory T-cell surface receptor; adding to the well a single or multiple peptide epitopes that binds to the cell surface MHC molecules to be presented for recognition by cognate T cells; the stimulatory signal could also be delivered by live target cells that display peptide epitope(s); wherein the recognition of stimulatory of pMHC by the peptide specific T cells leads to increase of intracellular $Ca^{2+}$ level and fluorescence intensity in the responding T cells, which is then identified after the subtracting fluorescence intensity for every T cell before and after the addition of the peptide antigens; measuring changes in number of an individual T cells with increased intracellular fluorescence as function of time provides the kinetic curve of the TCR-mediated $Ca^{2+}$ signaling.

A method for calculating the number of responding T cells in a sample comprising: coating glass bottom surface of 96-well plates with an agent capable to bind either an antibody or other capturing proteins; washing said plates free of unbound reagents, wherein the plates were covered with an antibody or other capturing proteins specific for non-stimulatory receptor on the T-cell surface that do not interfere with the induction of T-cell response; blocking the plates with BSA solution; capturing cloned T cell or freshly purified T cells from donor's PBMC labeled with $Ca^{2+}$ sensitive fluorophore; measuring background of intracellular fluorescence for every cell by means of wide field fluorescent microscopy; adding to the wells an antigenic peptide of interest or live target cell presenting potential peptide epitope; measuring fluorescence intensity for every cells in the same fields before and after addition of the stimuli at several time points; stimulating cells with ionomycin and non-stimulatory or "self" peptides serve as positive and negative controls, respectively; comparing intracellular fluorescence in individual cells before and after peptide or live target cells injection using MetaMorph software wherein the number of cells that remain fluorescent in each analyzed field are quantified to calculate the total number of the responding cells per $10^6$ cloned T cells or donor's PBMC.

A method for detecting and quantification of the frequency of T cells to multiple antigenic peptide epitopes comprising measuring intracellular $Ca^{2+}$ signaling in individual T cells that are labeled with $Ca^{2+}$ sensitive fluorophore; wherein said T cells are placed on the glass bottom of a well, covered with antibodies or other capturing proteins specific for non-stimulatory T cells' surface receptors and wherein a peptide antigens are injected into the well and the peptide binds to MHC molecules on the T-cell surface, wherein an increase in the intracellular concentration of $Ca^{2+}$ in responding T cells leads to rise in intracellular fluorescence that is detected by fluorescent microscope.

A method to characterize cell surface markers on T cells with the specificity of interest in order to determine a stage of T-cell differentiation comprising: Immobilizing freshly isolated CD8 T cells labeled with $Ca^{2+}$ sensitive fluorophore and antibodies labeled with non-overlapping fluorophore against cell surface markers of interest on the glass bottom of a well, covered with capturing antibody or a capturing protein that bind to non-stimulatory T-cell surface receptor; measuring background intracellular fluorescence for every cell of the T-cell monolayer and detecting individual T cells that express cell surface markers of interest by means of wide field fluorescent microscopy; calculating total number of cells that express cell surface markers of interest per $10^6$ CD8 T cells; adding to the wells an antigenic peptide(s) to be tested; comparing intracellular fluorescence in individual cells before and after peptide injection using MetaMorph software wherein the number of cells that remain fluorescent in each analyzed field are quantified to calculate the total number of the responding CD8 T cells per $10^6$ cells; and calculating the fractions of responding cells that do or do not express surface markers of interest.

In a further embodiment, disclosed is a method for measuring the frequency of responding T cells with the specificity of interest using live target cells presenting peptide(s) of interest or nanoparticles carrying soluble peptide-MHC ligands or any other peptide-MHC oligomers to stimulate T cells recognizing these ligands comprising: Immobilizing T cells labeled with $Ca^{2+}$ sensitive fluorophore on the glass bottom of a well, covered with capturing antibody or a capturing protein that bind to non-stimulatory T-cell surface receptor; measuring background of intracellular fluorescence for every cell of the T-cell monolayer by means of wide field fluorescent microscopy; adding to the wells live target cell presenting peptide(s) of interest or nanoparticles bearing various peptide-MHC or any other peptide-MHC oligomers that ought to be tested; measuring fluorescence intensity for every cells in the same fields after the exposure of T cells in the T-cell monolayer to the above stimuli; comparing intracellular fluorescence in individual cells before and after the stimulation using MetaMorph software wherein the number of cells that remain fluorescent in each analyzed field are determined as responding cells; and calculating the total number of the responding cells per $10^6$ cloned T cells or donor's PBMC.

A further embodiment is directed to a method to determine the frequency and functional activity of antigen-specific CD8 T cells from human PBMC through an assay based on measurement of T-cell intracellular $Ca^{2+}$ signaling induced in response to antigen recognition by T-cell receptor comprising: immobilizing freshly isolated CD8 T cells from human PBMC either intact or labeled with $Ca^{2+}$ sensitive fluorophore on the glass bottom of a well, covered with capturing antibody or a capturing protein that bind to non-stimulatory T-cell surface receptor; adding to the wells unlabeled or fluorescently labeled peptide-MHC proteins assembled on nanoparticles or any other peptide-MHC oligomers to detect antigen-specific T cells and/or to induce $Ca^{2+}$ signaling in the responding T cells; wherein the recognition of unlabeled stimulatory pMHC by the specific T cells labeled with Calcium fluorophore leads to increase of intracellular $Ca^{2+}$ level and fluorescence intensity in the responding T cells, which is then identified after the subtracting fluorescence intensity for every T cell measured before the addition of the stimulatory peptide-MHC oligomers. The binding of fluorescently labeled cognate pMHC to unlabeled T cells will identify both responding and non-responding T cells specific for the same peptide-MHC ligands; and calculating a fraction of responding T cells with the specificity of interest.

In a further embodiment we compared 3D plot images illustrating $Ca^{2+}$ responses of the T cells to a strong agonist and non-stimulatory peptide to reiterate the ability of the assay to detect responding T cells. In addition, we compared 3D plot images illustrating $Ca^{2+}$ responses of the T cells at high ($10^{-4}$ M) and suboptimal ($10^{-8}$ M) peptide concentrations. The comparison showed that the decrease of the response magnitude at lower peptide concentration was due to lower amplitude of the responses of individual cells, but not due to the changes in the number of the responding cells.

A further embodiment comprises an express method allowing measuring kinetics of $Ca^{2+}$ flux in responding to antigenic peptides on T cells that form monolayer on the glass surface. Freshly isolated T cells labeled with $Ca^{2+}$ sensitive fluorophore are immobilized on the glass bottom of a well covered with non-stimulatory antibody specific for a cell surface receptor. Peptides of interest that are added to the T cell monolayer bound to the MHC molecules presented for recognition by cognate T cells. The recognition of stimulatory of pMHC by the peptide specific T cells leads increase of $Ca^{2+}$ and fluorescence intensity in the responding T cells, which could then be identified after the subtracting fluorescence intensity for every T cell before and after the addition of the peptide antigens. Measurements of the number of responding cells as a function of time characterize the kinetics of the $Ca^{2+}$ flux in responding T cells. Accordingly, a time plot can be utilized to determine the kinetics of the $Ca^{2+}$ response for a particular antigen.

A further embodiment is directed to a method of calculating the response rate of a T cells comprising: coating a glass bottom plates with Poly-L-Lysine and, after washing free of unbound reagents, the plates were covered with antibody specific for non-stimulatory receptor on the surface T cells that do not interfere with T cell responses. The plates were blocked with BSA solution prior to addition of T cells. We utilize cloned T cell or freshly purified T cells from donor's PBMC labeled with $Ca^{2+}$ sensitive fluorophore. The capturing of the T cells by the immobilized antibody was facilitated by brief centrifugation at 700 g and unbound cells were removed by gentle washing. We analyze the quality of the T-cell monolayer, which formed on the glass surface, and measured background intracellular fluorescence for every cell by means of wide field fluorescent microscopy. We then add to the wells an antigenic peptide of interest to be tested and measure fluorescence intensity for every cells in the same fields as before at several time points. Stimulating cells with ionomycin and non-stimulatory or "self" peptides serve as positive and negative controls, respectively. We compare cellular fluorescence in individual cells before and after peptide injection using MetaMorph software. This allow us to quantify the number of cells that remain fluorescent in each analyzed field and to calculate the total number of the responding cells per $10^6$ cloned T cells or donor's PBMC.

A method for detection of the frequency of T cells to multiple antigenic peptide epitopes comprising: Coating a well with poly-L-Lysine or, in further embodiments, optically clear plastic surface can be used that is modified with other chemical agents capable to bind antibodies or other capturing proteins; capturing TS2/4 antibody with said poly-L-Lysine, or in further embodiments, streptavidin can be utilized to capture biotinylated antibody. Furthermore, any other capturing molecules specific to T cell's surface that do not interfere with Ca2+ flux can be utilized; thereafter, adding cloned CD8 T cells with known specificity (OR polyclonal CD8 T cells) and labeling each with $Ca^{2+}$ fluorophore Fluo-4 and adding the T cells to the wells, or, in further embodiments, other cells, including CD4 T cells or gamma/delta T cells can be added to the wells, or, in further embodiments, the cells can be labeled with any Ca2+ sensitive fluorophore and wherein changes in bioelectric properties of T cells can be measured.

A method for quantification of T cells specific to multiple antigenic peptide epitopes or other ligand recognizable by T cells. In certain embodiments, quantification can be live target cells loaded with peptides, or any antigen presenting cells that display naturally processed peptides such as tumor associated antigen. Furthermore, it could be unknown antigens presented at the cell surface.

A method for determining functional T cell quality by analyzing $Ca^{2+}$ response over time, based on the parameters of any one of the methods described above. In certain embodiments, the analysis may be of T cell surface markers or cytokine (intracellular or released) or analysis of TCR sequences of the responding cells.

These methods are particularly suited for analyzing frequency of T cells recognizing tumor associated antigens within tumor infiltrating lymphocytes (TIL) using either tumor-associated peptide epitopes or antigen-presenting cells sensitized with tumor associated peptide epitopes or live tumor cells. In addition, to measuring frequency of CD8 T cells with desired specificity, the frequency of CD4 T cells recognizing peptide-MHC-II ligands will also be measured.

A method for determining the efficiency of pathogen-specific T cells comprising: preparing a continuous monolayers of freshly isolated T cells labeled with Ca2+ sensitive fluorophore; adding a suspension of tumor cells could be used to detect tumor specific T cells within the monolayer; measuring Ca2+ responding T cells in the monolayer and to measure the kinetics of Ca2+ flux; and determining the frequency and efficiency of pathogen-specific or tumor-specific T cells within the monolayers.

In each of the embodiments described above, wherein the frequency and efficiency of pathogen-specific or tumor-specific T cells are compared to a control. In certain embodiments, the control is derived from a sample of T cells from a health patient. In certain other embodiments, the control is a predetermined number derived from a plurality of samples from healthy patients.

A method for predicting efficacy of a treatment and a clinical outcome comprising: analyzing the frequency and the efficiency of the responding T cells; wherein said frequency and efficiency will provide an essential information regarding status of the immune response against pathogens or cancer in order to predict the outcome of the infection or cancer spread as well as to choose appropriate treatment for tested individuals; wherein the latter will have significant impact on the cost of treatment and will increase survival rate of the patients. In particular embodiments of the method, the frequency and efficiency of the responding T cells are compared to a control; wherein an efficiency within one standard deviation of the control indicates a functioning immune system; and wherein an efficiency is reduced by more than one standard deviation of the control indicates a compromised immune system. In certain embodiments, indication of a compromised immune systems requires administering to a patient with said comprised immune system a composition suitable for treating a suspected virulent such as CMV.

A kit for measuring the frequency of T cell response comprising: a premade microtiter plates or ibidi chambers; a Ca2+ sensitive fluorophore; a predetermined set of antigenic peptides; and a control.

Additional features and embodiments will be apparent to one of ordinary skill in the art upon consideration of the following detailed description of preferred embodiments and descriptions of the best mode of carrying out the invention.

BRIEF DESCRIPTION OF THE DRAWINGS

FIGS. 3A-3E depict graphical representations of $Ca^{2+}$, wherein FIGS. 3A, 3B, and 3C depict images and graphical representation of $Ca^{2+}$ flux induced by strong agonist peptide in Fluo-4 labeled cloned T cells that form monolayer at the glass bottom of a well. FIGS. 3D and 3E show 3D plot images illustrating $Ca^{2+}$ responses of the T cells to a non-stimulatory and a strong agonist peptides.

DETAILED DESCRIPTION OF THE PREFERRED EMBODIMENTS

Figure 1:
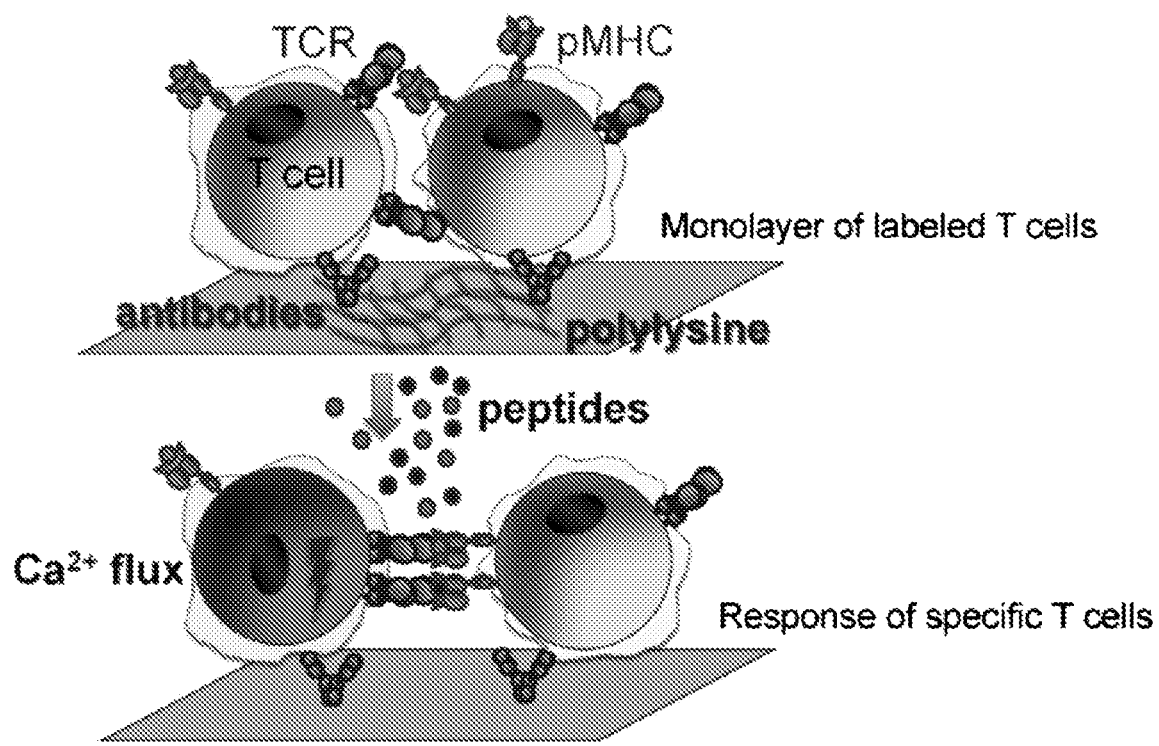
FIG. 1 provides a depiction of a schematic flow of an embodiment of the invention disclosed herein.

The embodiments of the invention and the various features and advantages thereto are more fully explained with references to the non-limiting embodiments and examples that are described and set forth in the following descriptions of those examples. Descriptions of well-known components and techniques may be omitted to avoid obscuring the invention. The examples used herein are intended merely to facilitate an understanding of ways in which the invention may be practiced and to further enable those skilled in the art to practice the invention. Accordingly, the examples and embodiments set forth herein should not be construed as limiting the scope of the invention, which is defined by the appended claims.

As used herein, terms such as "a," "an," and "the" include singular and plural referents unless the context clearly demands otherwise.

As used herein, the term "CAFlux" refers to the novel assay described herein.

The frequency of pathogen-specific and tumor-specific T cells and their functional activity reflect the effectiveness of immune responses and can serve as useful diagnostic and prognostic indicators. For example, the kinetics of Ca2+ flux determines the kinetics of cytolytic granule (poison pill) release and, consequently, the kinetics of target cell destruction by cytotoxic lymphocytes. The latter is very important factor that helps T cells to win the race against the virus or cancer spread. Therefore, faster kinetics of Ca2+ flux suggest the ability of tested T cells to fight very effectively viruses and cancer, while T cell responding with slow Ca2+ kinetics are less efficient. The latter constitutes the prognostic value of the approach. If a patient has T cells are responding with the faster kinetics, it is likely that this patient will fight corresponding virus and cancer cells more efficiently. Having this information, the doctor could make informed decision regarding the therapy that is likely needed in each particular case: for instance, strong ability to fight the virus would not requires application of very expensive anti-viral therapy.

It is, therefore, essential to follow T-cell responses during infection, cancer, vaccination or hematopoietic stem cell transplantation. Responding T cells at various differentiation stages have different functionalities and produce distinct spectrums of cytokines. However, it is important to detect T cell responses with the specificity of interest regardless of their stage of differentiation and functional activities that may serve as a better indicator of the quality of immune response.

Increase in intracellular concentration of $Ca^{2+}$ upon T cell activation appears to be a universal marker of responding T cells. Although $Ca^{2+}$ flux measuring by Flow Cytometry works well for T cell clones and lines, analysis of $Ca^{2+}$ response in heterogeneous population of T cells with a small proportion of T cells with the specificity of interest has proved to be difficult due to large differences in the fluorescent intensity of individual cells. The approach described herein, permits determining the concentration of intracellular $Ca^{2+}$ in each individual T cell before and after stimulation providing a unique opportunity to directly identify each responding T cell that significantly increase the sensitivity and utility of the assay as compared to all others available assays thus far.

In addition to accurate and rapid evaluation of the frequency of pathogen-specific and tumor-specific T cells, the approach also permits measuring the kinetics of intracellular Ca' accumulation that characterizes the quality of T cell responses and reflects the effectiveness of immune responses that can serve as useful diagnostic and prognostic indicator. Currently, frequencies of pathogen-specific T cells produced by pMHC/tetramers staining and ELISpot assay very often do not correlate with clinical outcomes. Because the CaFlux assay detects only functional T cells, we expect that analysis of the frequency of T cells by the assay will reveal a much better correlation with clinical outcomes and will provide information regarding efficacy of T-cell responses.

To overcome the drawbacks in the prior art, we have developed an approach to measure the $Ca^{2+}$ response in individual T cells by means of fluorescent microscopy. Specifically, we have utilized CD8+ T cells labeled with $Ca^{2+}$-dependent fluorophore and analyzed intracellular fluorescence of these T cells in monolayers before and after stimulation with specific antigenic peptides. Subtraction of intracellular fluorescent intensity measured prior to and after the stimulation readily revealed the small subpopulation of responding T cells and allowed determination of their frequency. Using T cell clones, we optimized the assay parameters and determined the limit of detection and sensitivity of the approach. We also determined the number of different peptides capable of eliciting T cell responses in a single round of analysis. To demonstrate the usefulness of the approach, we analyzed frequency of CMV-specific T cells from peripheral blood derived from healthy donors and patients who underwent hematopoietic stem cell transplantation (described in Results below). The results confirmed the potential diagnostic and prognostic values of the proposed approach.

In the CaFlux assay we analyze intracellular $Ca^{2+}$ flux in responding T cells. Virtually each functional T cell shows rise in intracellular $Ca^{2+}$ level after antigen recognition. Thus, it is possible to enumerate antigen-specific T cells independently of their phenotypes and functional subtypes. It requires only 3-5 minutes to complete CaFlux assay. The presence of T cells with the specificity of interest will be simultaneously tested by measuring $Ca^{2+}$ signaling in these cells stimulated with predetermined mixture of antigenic peptides in one round of analysis.

The kinetics of $Ca^{2+}$ response reflects the efficiency of the antigen-specific T cells and could be used to estimate the efficacy of the immune response to particular antigen. Because rapid kinetics of $Ca^{2+}$ response is linked to rapid target cell destruction by cytotoxic T cells, the ability to kill faster determines efficiency of T cells, and the efficiency of T cells influences efficacy of the immune response against pathogens and cancer. The comparisons of CAFlux to Tetramer and ELISpot assays are summarized in Table 1 (the most significant advantages are in bold).

TABLE 1

A comparison of CaFlux Assay with ELISpot and pMHC tetramer:

| Parameter | CaFlux | Tetramer | ELISpot |
| --- | --- | --- | --- |
| What is measured? | $Ca^{2+}$ Signaling, a universal parameter of responding T cells | TCR specificity | Secreted cytokines |
| Time of the parameter measuring | 2-3 min (microscope) | 2-3 min (FACS) | 24-48 hr of cultivation |
| Type of the T cells | Functional T cells plus the ability to evaluate the efficiency of T cell response | Functional plus anergic (non-responsive) T cells | T cells producing defined cytokine, anergic T cells may be activated during assay accounting for pseudo positive T cells |
| Frequency | A few cells per $10^4$ CD8 T cells | A few cells per $10^4$ CD8 T cells | A few cells per 2-4 × $10^5$ PBMC*[)] |
| APC | Not required but can be used | Not required | Required |
| Number of antigen specific peptides per assay | 1-100 peptides restricted by a single or multiple alleles | A few | 10-20 peptides |
| Drawbacks | Required CD8 T cell isolation | Require production of pMHC protein for each peptide; quantifies anergic T cells | Do not define distinct T cell subsets; quantifies anergic T cells |

*[)]because the fraction of CD8 T cells in PBMC correspond to 5-10%, the sensitivity of the assay is comparable with pMHC tetramer and CaFlux assays.

The assay makes it possible to reliably determine the frequency of functional pathogen-specific peripheral blood T cells with wide range of avidities during immune responses to infection or vaccination or tumor progression. Such data will have an important prognostic value for a disease outcome or effectiveness of pathogen-specific vaccines or immune system disorder. We have shown successful application of CaFlux assay for measuring frequencies of CMV-specific T cells in PBMC of normal donors and after CMV reactivation in a patient who underwent bone marrow transplantation. Particularly, the assay revealed differences in the kinetics of $Ca^{2+}$ flux in T cells from normal donors and the patient earlier after bone marrow transplantation.

In further embodiments, the assay can be further adopted (i) to measure the frequency of T cells producing cytokines of interest, (ii) to characterize cell surface markers on the T cells in order to determine T-cell stage of differentiation, and (iii) to measure the frequency of responding T cells with the specificity of interest using live target cells presenting peptide(s) of interest or nanoparticles carrying soluble peptide-MHC ligands to stimulate T cells recognizing these ligands. This will be particularly valuable for analyzing frequency of T cells recognizing tumor associated antigens within tumor infiltrating lymphocytes (TIL) using either tumor-associated peptide epitopes or antigen-presenting cells sensitized with tumor associated peptide epitopes or live tumor cells. In addition, to measuring frequency of CD8 T cells with desired specificity, the frequency of CD4 T cells recognizing peptide-MHC-II ligands will also be measured.

Accordingly, to determine the frequency and functional activity of antigen-specific CD8 T cells from human PBMC, we have developed an assay based on measurement of T-cell intracellular $Ca^{2+}$ signaling induced in response to antigen recognition by T-cell receptor. We analyzed intracellular Ca2+ flux in T cells, a measurement that is widely used to detect ligand-stimulated T cells and study receptor-mediated signaling (Grafton, G. & Thwaite, L., 2001, Immunology, 104: 119-126; Omilusik, K. et al., 2011, Immunity, 35: 349-360). However, in the assay we have developed, cognate and non-cognate peptide-MHC-I ligands on the surface of target cells effectively cooperate in the induction of intracellular $Ca^{2+}$ flux allowing us to utilize many different antigenic peptides to test the presence of all T cells recognizing these peptide ligands simultaneously in a single round of analysis.

This unique capability of the assay steams from that fact that each tested peptide added in a peptide mixture to the T-cell monolayer could function as a cognate peptide for some T cells, while other peptides would behave as non-stimulatory or self-like peptides. Because T cells in the monolayer present peptide to each other, antigenic peptides restricted by different MHC alleles would function as self-like peptides. To this end, all T cells that are specific for each of the tested peptides are expected to respond to their respective cognate peptides providing that the concentration of these peptides is sufficient. Using T cell clones with known specificity for an agonist peptide, we have found that T cells specific for this peptide could still respond to the peptide being diluted by 100-fold with a mixture of non-stimulatory peptides. This suggests that up to 100 peptides can still be analyzed simultaneously in one round of the assay.

The changes in intracellular $Ca^{2+}$ are usually measured by flow cytometry. The flow cytometry approach is widely used but doesn't allow comparison of the same cell before and after stimulation to avoid false positive results. We measured intracellular $Ca^{2+}$ in individual CD8 T cells that were immobilized on a glass surface to form a monolayer enabling the cells to present antigenic peptide to each other. This provided a significant increase in the sensitivity and utility of the assay that is required to analyze frequency of pathogen-specific T cells in clinical setting. The newly developed assay made it possible to reliably determine the frequency of human pathogen-specific peripheral blood CD8 T cells that demonstrated Ca2+ responses of different kinetics. The assay has an important diagnostic and prognostic value analyzing infection outcome and effectiveness of pathogen-specific vaccines.

Material and Methods

T Cell Clones and their Maintenance

HIV- and Flu-specific human CD8+ T cell clones, termed 68A62 and CER43, were kindly provide by Bruce Walker and Antonio Lanzavecchia, correspondingly. These T cells recognize ILKEPVHGV (IV9; SEQ ID NO: 1) and GILGFVFTL (GL9; SEQ ID NO: 2) peptides, respectively, both presented by HLA-A2 MHC class I (Beal, A. M. et al., 2009, Immunity 31: 632-642; Anikeeva, N. et al., 2005, Proc. Natl Acad. Sci. USA, 102: 6437-6442; Beal, A. M. et al., 2008, J. Immunol. 181: 4815-4824). 115iX is a CD8+ T cell line developed from CTL D3 (Kalams, S. A. et al., 1994, J. Exp. Med., 179: 1261-1271; Brander, C. et al., 1998, J. Clin. Invest., 101: 2559-2566; Anikeeva, N. et al., 2003, J. Immunol. Methods 277: 75-86) as a result of spontaneous mutation in its TCR J3 chain resulting in lost of specificity for its natural ligand (Somersalo, K. et al., 2004, J. Clin. Invest., 113: 49-57). These were used as T cells with irrelevant specificity. After stimulation with a mixture of allogeneic PBMC and IL2 the cells are typically used in resting stage, 12-17 days after the stimulation.

Labeling of T Cells with Calcium Indicator $10^6$ cells in 1 ml of PBS were loaded with Fluo-4 (Life Technologies) at 2-4 µM for 30 min at 37° C. in the presence of 0.02% pluronic acid F-127 and 4 mM Probenecid. The cells were washed free of unreacted reagents and incubated at 37° C. for additional 30 min. The cells were then re-suspended in the assay buffer (Dulbecco's PBS containing 1 mM CaCl2, 2 mM MgCl2, 5 mM glucose, and 0.025% BSA) and used for Ca2+ flux analysis.

Magnetic Sorting of CD8+ T Cell

CD8 T cells were purified from frozen PBMC using MACS Cell Separation Technology according to manufacturer instruction (Miltenyi Biotec).

Antibodies and Peptides

Hybridoma producing TS2/4 anti-LFA-1 antibodies was purchased from ATCC. The antibody was purified from culture supernatant by affinity chromatography on protein A Sepharose as described elsewhere (Beal, A. M. et al., 2008, J. Immunol. 181: 4815-4824). GL9 peptide from the influenza matrix protein was synthesized by Research Genetics, Inc and IV9 peptide from HIV reverse transcriptase Tsomides, 1991 #167 was a gift from Herman Eisen (MIT).

Preparation of T-Cell Monolayers

Glass bottom of 96 well MatTec plates was covered with poly-L-Lysine (Sigma, mol wt>300,000) at 0.1 mg/ml for 1 hr at room temperature. After washing with DPBS and dd water, TS2/4 non-blocking mAb specific for LFA-1 were added to the plate at concentration 10 µg/ml overnight & 4° C. The wells were washed with DPBS, and $3 \times 10^5$ Fluo-4-labeled T cells in 100 µl of the assay buffer were added to each well. The plates were centrifuged for 700 g for one minute and were incubated for 30 min at room temperature prior to the imaging. Suspended cells were removed by gentle washing with assay buffer. The quality of T cell monolayer was assessed using bright field microscopy.

Induction and Measurements of $Ca^{2+}$ Flux in T Cells

To identify responding T cells we imaged T-cell monolayers before (background measurement) and after (response) addition of the stimulatory signal such as agonist peptide. The images of T-cell monolayers were taken at various exposure times using 10× or 20× objectives. In some experiments Ca2+ response was also initiated by ionomycin at 10 µg/ml to optimize exposure time (data not shown). The average intensity of images prior and after the T-cell stimulation at various time points and the numbers of individual responding cells per imaging field were determined by MetaMorph software.

Cytolytic Assay

Lymphoblastoid target cells JY ($5 \times 10^3$) were washed, $^{51}$Cr-labeled and then sensitized for one hour with various amounts of a peptide of interest in 150 µl R10 (RPMI-1640 containing 10% FCS). 68A62 CTL in 50 µl in of R10 were then added with a final assay volume of 200 µl. The assay was performed in 96-well round-bottomed plates at an effector-to-target ratio of 5:1. The plates were incubated for four hours in a $CO_2$ incubator at 37° C. and $^{51}$Cr release was measured in 100 µl of supernatant from each well. Percent specific lysis was determined as previously described in Sykulev, 1996 #209, Anikeeva, 2006 #1422; Beal, 2008 #2027.

Results

Principle of the Assay

All nucleated cells, including CD8 T cells that play essential role in virus-specific immunity, express MHC-I proteins. Thus, the T cells could recognize cognate peptide MEW ligand on their surface, get activated, and exercise effector functions against each other (Su, M. W.-C., et al., 1993, J. Immunol., 151: 658-667). This should allow identifying CD8 T cells with the specificity of interest in a population of the T cells isolated from PBMC. Antigenic peptides added to the cells rapidly bind to available MHC class I on the cell surface resulting in appearance of cognate peptide-MHC (pMHC) recognizable by TCR. The recognition of cognate pMHC leads to a rapid $Ca^{2+}$ flux in responding T cells. Thus, high density of CD8 T cells assembled into a monolayer on a glass surface provides an opportunity for T cells specific for a peptide of interest to mount rapid $Ca^{2+}$ response followed by sensitization of the T cells with cognate peptide added to the monolayer. $Ca^{2+}$ flux is detected by measuring increase of intracellular fluorescent intensity in responding T cells labeled with calcium-dependent fluorophore by means of fluorescent microscopy. The difference between initial intracellular fluorescence and the fluorescence measured after the peptide addition in individual cells with MetaMorph software reveals frequency of responding T cells in the monolayer. The analysis of kinetics of $Ca^{2+}$ increase provides the information about efficiency of T cell response to particular antigen.

Indeed, FIG. 1 depicts a schematic presentation of CaFlux assay. T cells form monolayers on the surface of the well covered with antibodies against T cell's surface receptors. A peptide antigen is injected into the well. The peptide molecules bind to MHC proteins expressed on the T cell surface to form recognizable pMHC ligands. Each T cells can serve as a target cells for neighboring T cells, but only rare antigen-specific T cell recognizes and responds to defined antigenic peptide used in the assay. Recognition events induce rise in the level of intracellular $Ca^{2+}$. To detect $Ca^{2+}$ influx, the T cells are labeled with Ca2+ sensitive fluorophore. The changes in fluorescent intensity in individual cells before and after peptide addition are measured with fluorescent microscopy to identify the frequency of responding T cells.

T-Cell Monolayer

Figure 2:
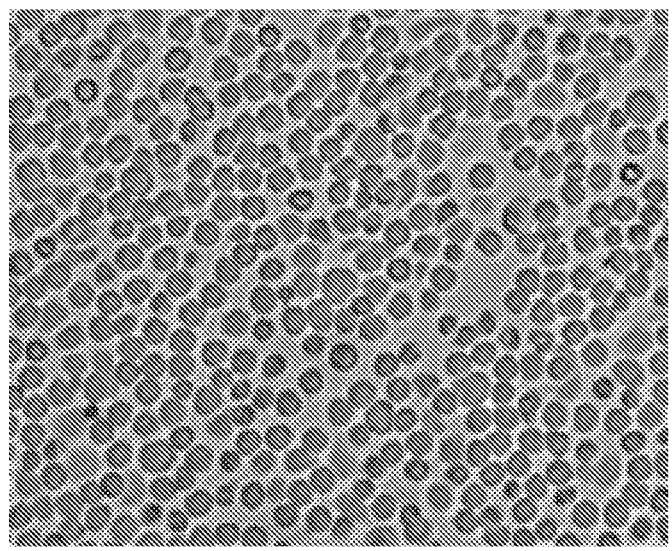
FIG. 2 depicts T-Cells attached to a glass surface.

Glass bottom of 96-well plates was covered with poly-L-Lysine to capture TS2/4 antibody recognizing LFA-1 adhesion receptor without blocking LFA-1 functional activity. Cloned CD8 T cells with known specificity or polyclonal CD8 T cells were labeled with Ca2+ fluorophore Fluor-4 and added to the wells. The quality of the T-cell monolayers was evident from analysis of bright field images of the immobilized T cells on the glass bottom of the plate. FIG. 2 depicts T cells attached to a glass surface form a tight monolayer ensuring direct contact of T cells with each other. Accordingly, FIG. 2 shows that T cells form a continuous monolayer allowing the T cells to contact each other, which is necessary for presentation and recognition of pMHC on one T cell by another T cell.

Induction and Analysis of Responding T Cells

To optimize the conditions of the assay, we utilized human CTL clones CER43 and 68A62 recognizing nucleoprotein-derived peptide GL9 from Influenza virus and HIV RT derived peptide IV9, correspondingly (Beal, A. M. et al., 2009, Immunity 31: 632-642; Anikeeva, N. et al., 2005, Proc. Natl Acad. Sci. USA, 102: 6437-6442; Beal, A. M. et al., 2008, J. Immunol. 181: 4815-4824). Both peptides presented to these CTLs are restricted by HLA-A2 protein.

Figure 3A:
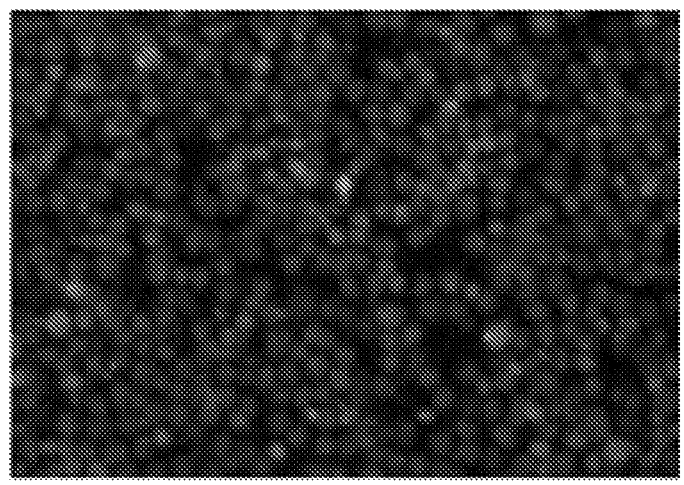
Figure 3B:
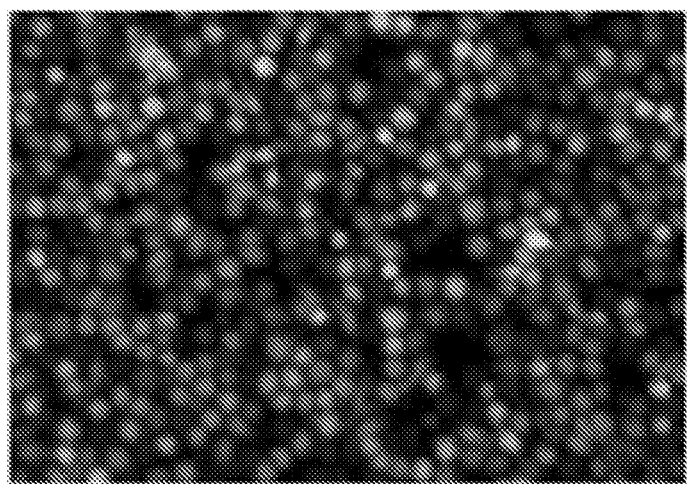
Figure 3C:
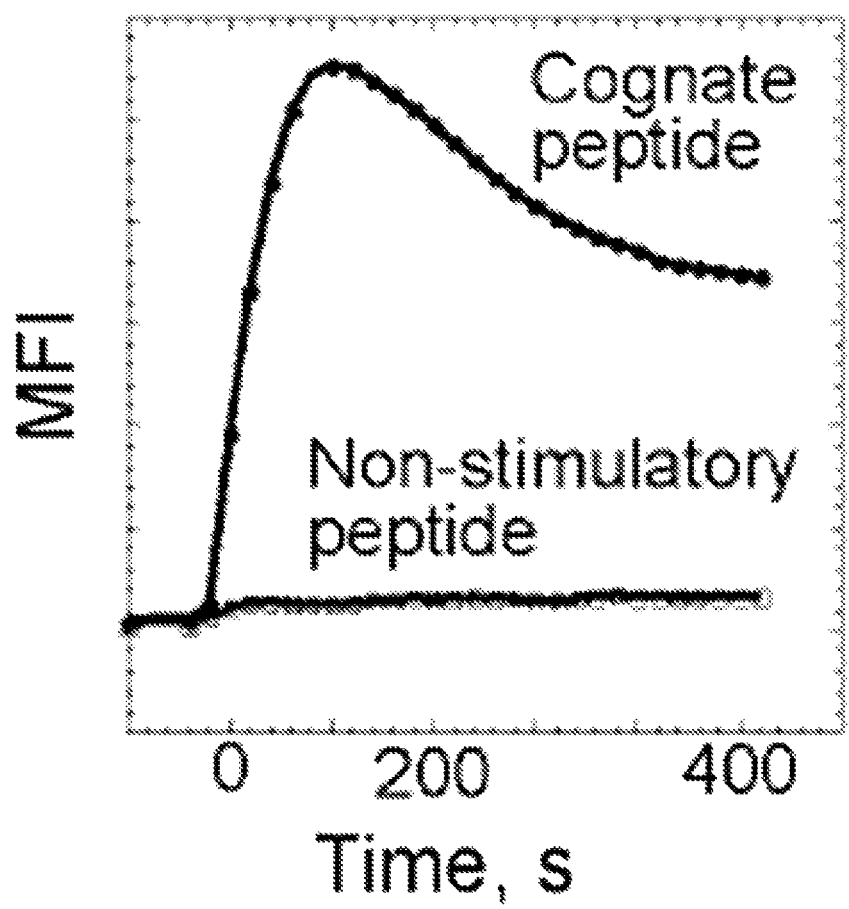

FIGS. 3A, 3B and 3C depict that addition of a strong agonist peptide to the monolayer of Fluo-4 labeled cloned T cells (A) induced intracellular $Ca^{2+}$ flux resulting in the increase of intracellular fluorescence (B). Maximum of mean fluorescence was achieved in 2-3 minutes following stimulation with a strong agonist peptide but not with non-stimulatory peptide (C).

Figure 3D:
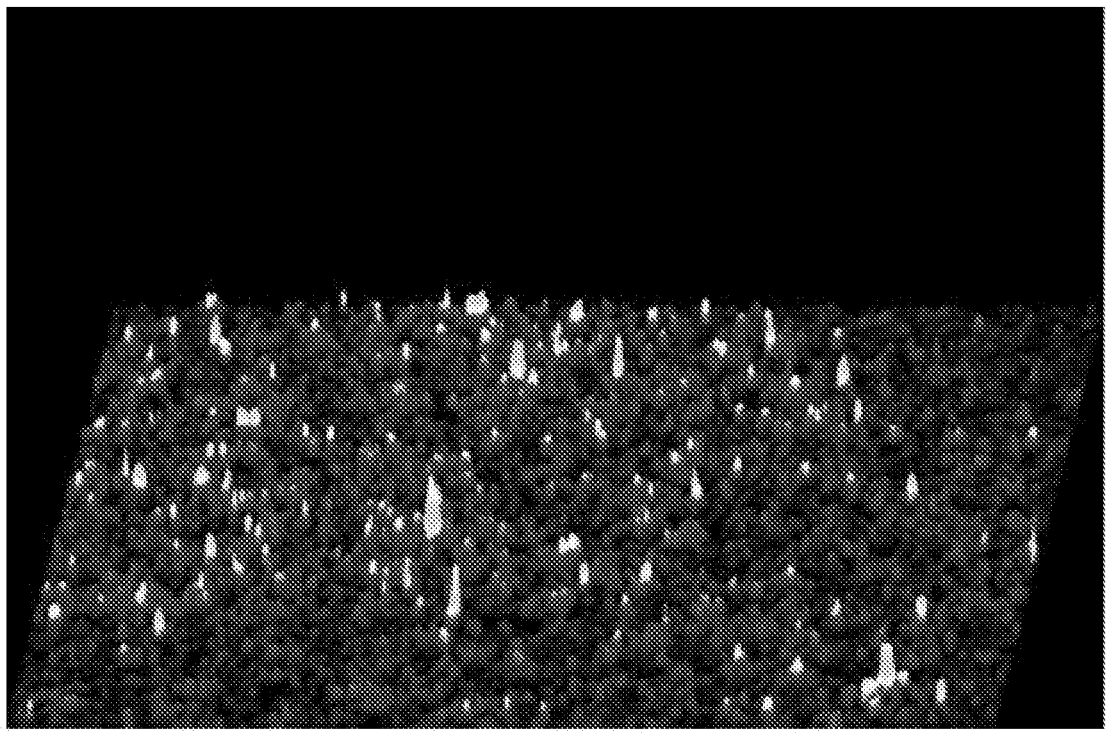
Figure 3E:
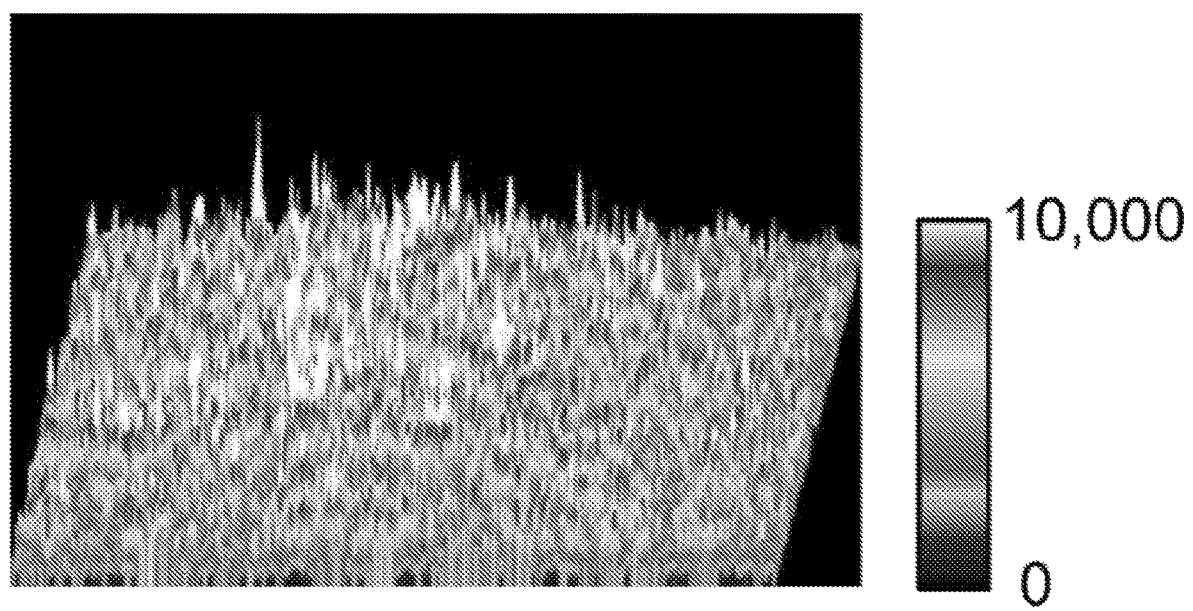

FIGS. 3D and 3E depict the topographical profiles or 3D plots of the image's fluorescent intensity level of individual cells before (D) and after (E) the stimulation. The fluorescent intensity is defined at a relative scale as depicted, wherein white and black colors correspond to maximal and minimal fluorescent intensities.

Figure 8:
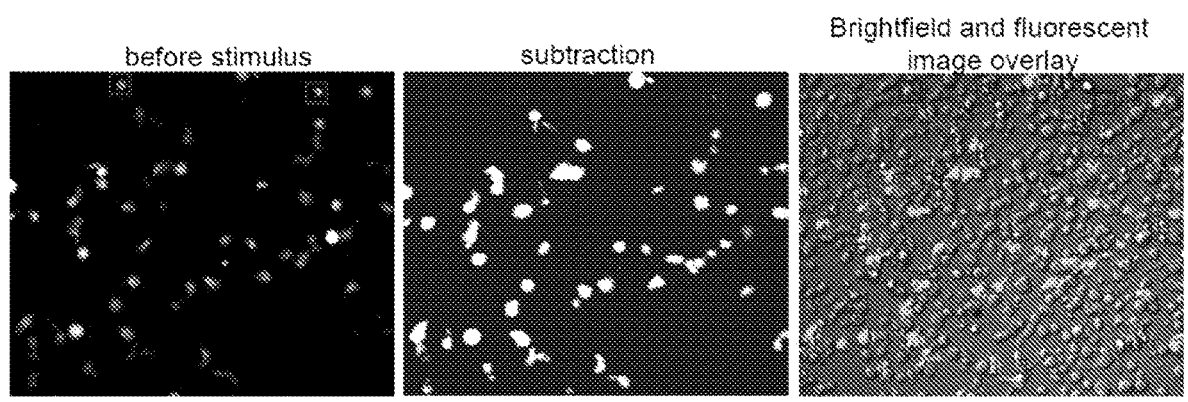
FIG. 8 depicts evaluation of the CAFlux assay sensitivity that is determined by the ratio of T cells responding to cognate peptide to the total number of antigen-specific T cells (in other words, usually some T cells of the total number of antigen-specific T cells, namely 2 out 57, did not responded; the latter could be due to various reasons, i.e. apoptosis, anergy, etc., that precluded responses of these T cells—this is to say that T cells in culture or those freshly isolated from PBMC always have some "defective" T cells and it is important to know what percentage of antigen-specific T cells could not be detected by the assay, which does not see unresponsive T cells).

Addition of cognate peptide to T cell monolayer resulted in a significant increase of intracellular fluorescent intensity of the T cells over the background indicative of $Ca^{2+}$ influx (FIGS. 3A and B). The $Ca^{2+}$ influx was observed in 90-95% of the T cells (FIG. 8). The addition of non-cognate peptide to the monolayer did not induce $Ca^{2+}$ signaling in tested T cells. Because calcium ions distributed all over cytoplasm, bleaching of the fluorescence was not evident allowing imaging dozens of fields after the signaling was initiated (FIG. 8).

FIG. 8 depicts evaluation of the CAFlux assay sensitivity that is determined by the ratio of T cells responding to cognate peptide to the total number of antigen-specific T cells (in other words, usually some T cells of the total number of antigen-specific T cells, namely 2 out 57, did not responded; the latter could be due to various reasons, i.e. apoptosis, anergy, etc., that precluded responses of these T cells—this is to say that T cells in culture or those freshly isolated from PBMC always have some "defective" T cells and it is important to know what percentage of antigen-specific T cells could not be detected by the assay, which does not see unresponsive T cells)

The time course of the CD8 T cell response to agonist peptide revealed two phases (FIG. 3C). The first phase is characterized by a quick rise of intracellular $Ca^{2+}$ concentration that reaches maximum followed by a slight decrease in the $Ca^{2+}$ level, while in the second phase the elevated level of intracellular $Ca^{2+}$ concentration sustained over a prolong time interval.

Figure 9:
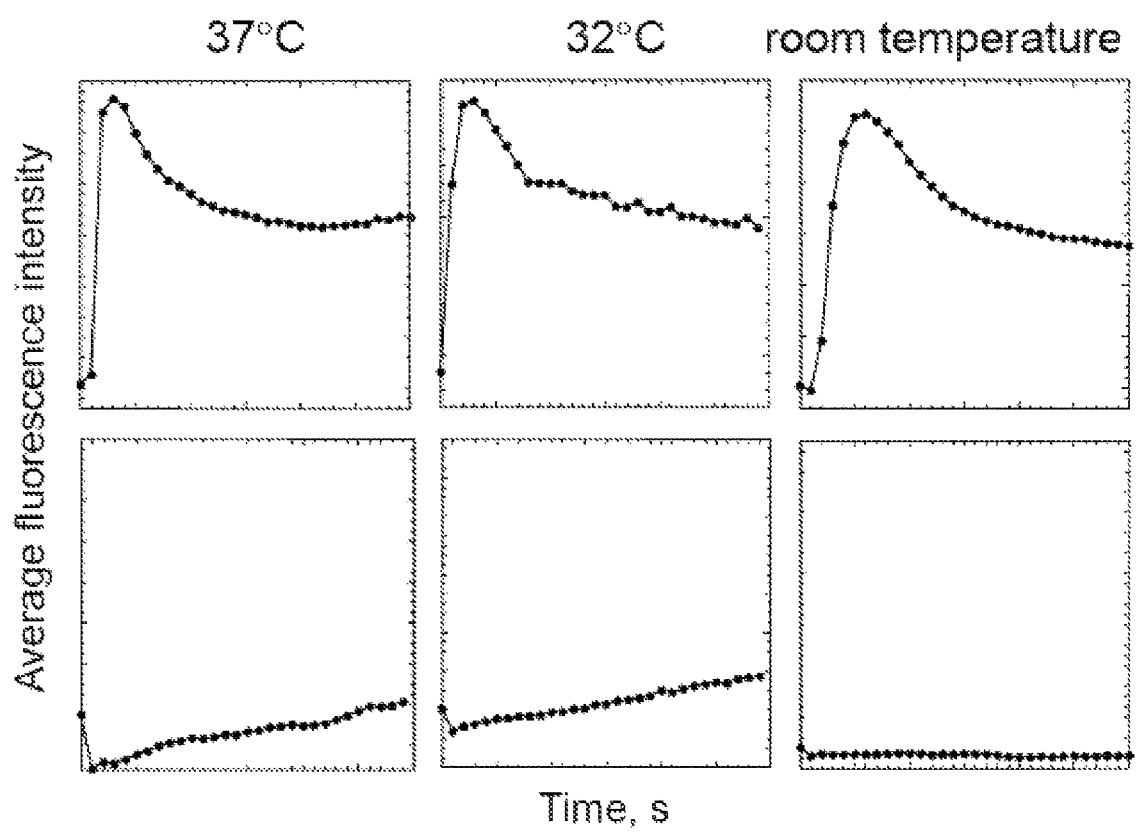
FIG. 9 depicts graphic representation of $Ca^{2+}$ response of cloned T cells at different temperatures.

As opposed to functional T cell responses such as production of cytokines or killing, $Ca^{2+}$ flux can be measured at room temperature simplifying the assay procedure and increasing the assay accuracy. FIG. 9 depicts a graphical representation of $Ca^{2+}$ response of cloned T cells at different temperatures. Although the kinetics of the response was slightly slower at room temperature, lowering temperature did not significantly influence the time window of the signal measurement and the ratio of maximal fluorescence intensity to the background fluorescence (FIG. 9).

Detection of Low Avidity T Cells

Figure 4A:
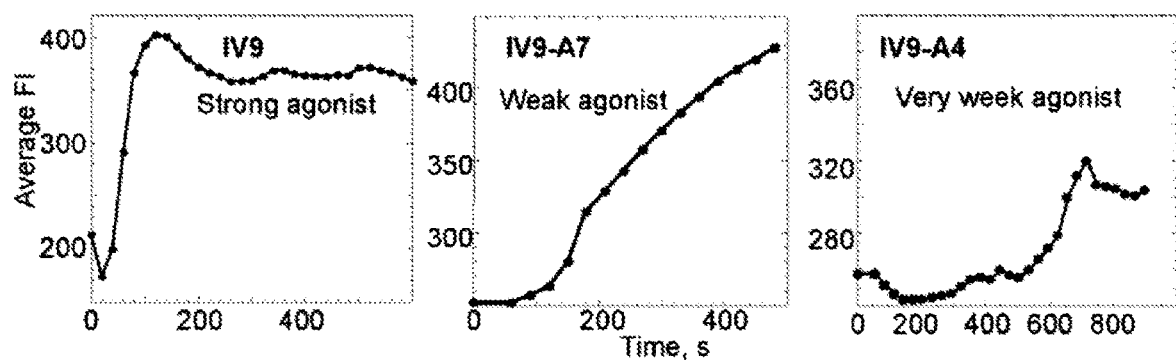
FIGS. 4A and 4B depict the comparison of efficiency of $Ca^{2+}$ and cytolytic response upon strength of TCR-mediated T cell stimulation.
Figure 4B:
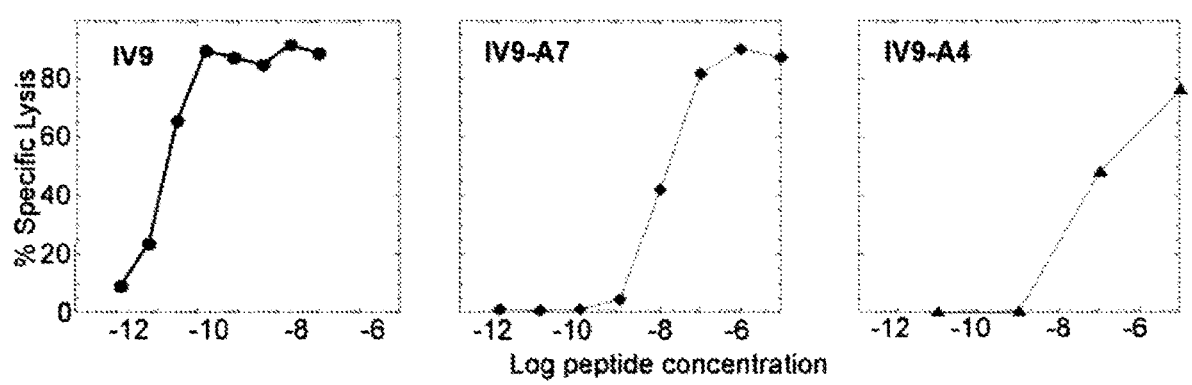

FIGS. 4A and 4B depict the dependence of the kinetics of $Ca^{2+}$ signaling and the efficiency of cytolytic response upon strength of TCR-mediated T cell stimulation. (A) Differences in time required for achieving maximum of calcium flux induced by peptide ligands of different strength. (B) Differences in concentration of the same peptides that are needed to achieve the same extent of specific target cells lysis by cloned CD8 T cells. The peptide concentrations that induce 50% specific lysis are indicated by arrows.

To evaluate the capability of the assay to detect low avidity T cells (T cells whose TCR binds to its natural ligand with a low intrinsic affinity), we resorted to IV9 peptide variants, namely, IV9-A7 and IV9-A4 peptides. All 3 peptides bind equally well to HLA-A2, but have different potency in CTL assay. Compared to IV9, the concentration of IV9-A7 and IV9-A4 peptides required to achieve similar extent of specific target cell lysis was 3 and 4 orders of magnitude higher, correspondingly (FIG. 4B). The two weak agonist peptides were still capable to elicit $Ca^{2+}$ flux in the monolayer of 68A62 CTL, but achieving the maximum of $Ca^{2+}$ increase in response to IV9-A7 stimulation was delayed to 10-15 minutes as compared to IV9 that induced maximum of their response within 2-3 minutes following stimulation (FIG. 4A). The response to a very weak agonist V9-A4 was barely detectable (FIG. 4A). The kinetics of calcium signaling was in accord with killing potency induced by the same peptides.

Minimal Required Peptide Concentration

Figure 5A:
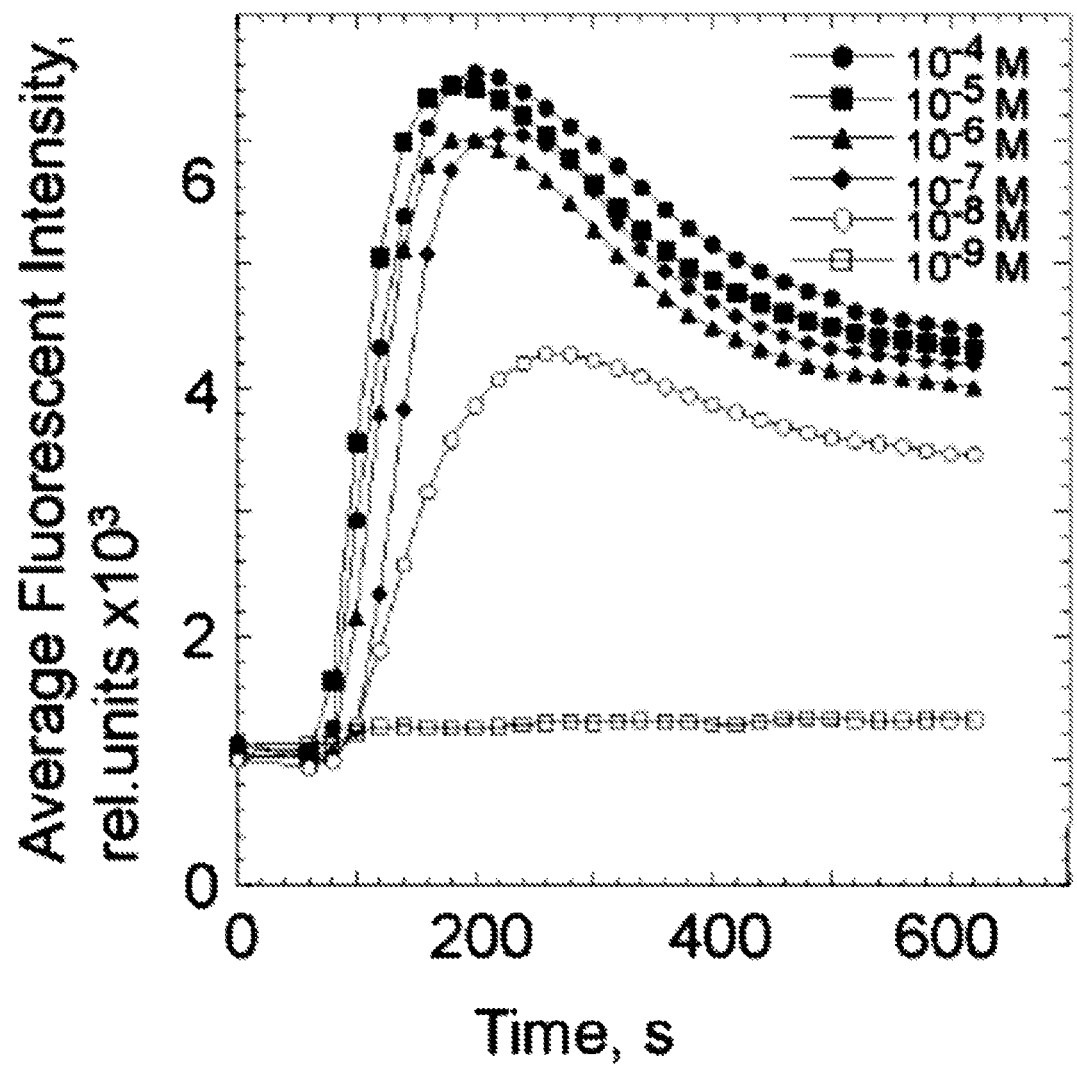
FIGS. 5A, 5B, and 5C depict the sensitivity to $Ca^{2+}$ and cytolytic responses induced by a strong agonist peptide at different concentrations.
Figure 5B:
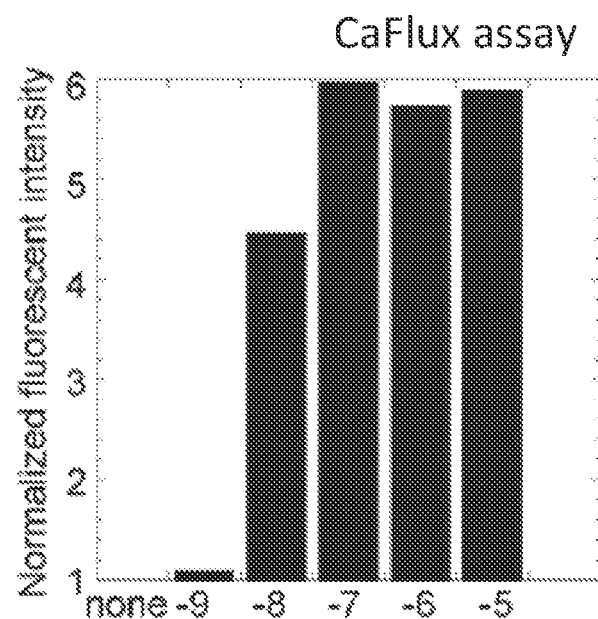
Figure 5C:
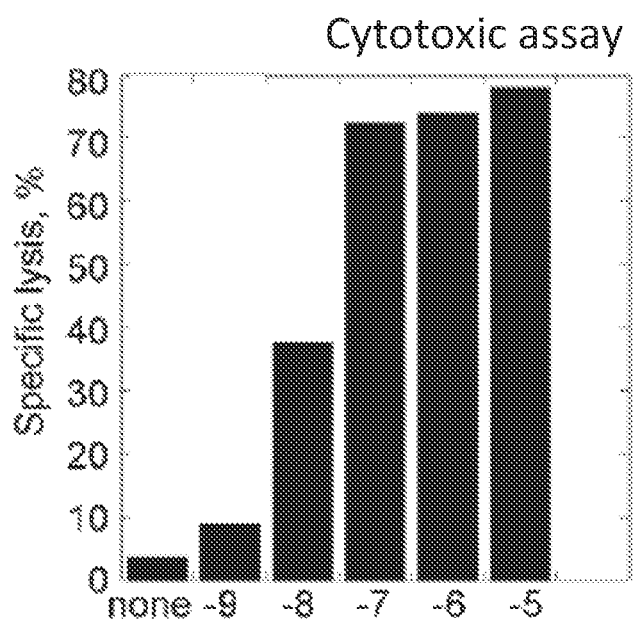

FIGS. 5A-5C depict the sensitivity of $Ca^{2+}$ and cytolytic responses induced by a strong agonist peptide. (A) The dynamics and magnitude of calcium response by CD8 T cells stimulated by a strong agonist peptide at various concentrations. The dependence of the magnitude of calcium (B) and cytolytic (C) responses upon the concentration of a strong agonist peptide.

To determine minimal peptide concentration that is required to detect specific T cells, assays were performed using various concentrations of a strong agonist peptide. FIG. 5A shows the dependence of the calcium response by T cells at peptide concentrations ranging from $10^{-4}$ M to $10^{-9}$ M. The time courses of $Ca^{2+}$ influx were very similar within the range of from $10^{-4}$ M to $10^{-7}$ M, and the peptide concentration of $10^{-8}$ M appeared to be minimal required concentration in induce detectable response. Comparison of the sensitivity of $Ca^{2+}$ flux with that of the cytolytic activity revealed that both responses have very similar sensitivity (FIGS. 5B and C). This is consistent with our previous findings showing that the magnitude and kinetics of $Ca^{2+}$ signaling control the efficiency of target cell lysis by CTL (Beal, A. M. et al., 2009, Immunity 31: 632-642. Sykulev, Y. 2010, Sci. Signal. 3: pe50).

Number of Specific T Cells Detected in a Single Round of CaFlux Assay

We next tested the ability of CaFlux assay detecting T cell responses to multiple peptide epitopes restricted by the same allele in one round of the assay. Because T cells in the monolayer present peptide to each other, testing antigenic peptides restricted by different MHC alleles would not expected to cause any problem. Each peptide in a mixture of several test peptides added to the monolayer of T cells isolated from peripheral blood could function as a cognate peptide for some T cells, while other peptides would behave as non-stimulatory or self-like peptides. To this end, all T cells that are specific for each of the tested peptides are expected to respond to their respective cognate peptides if the concentration of these peptides is sufficient. We chose Flu-derived peptide GL9 diluted in a mixture of non-stimulatory (self-like) peptides at 1:10 and 1:100 ratios. We then determine whether the diluted GL9 was still capable to induce $Ca^{2+}$ flux in CER43 T cells. The number, which defines the fold excess of non-stimulatory peptides, is essentially equal to the number of peptides that could be successfully tested in a single round of the assay.

Figure 6:
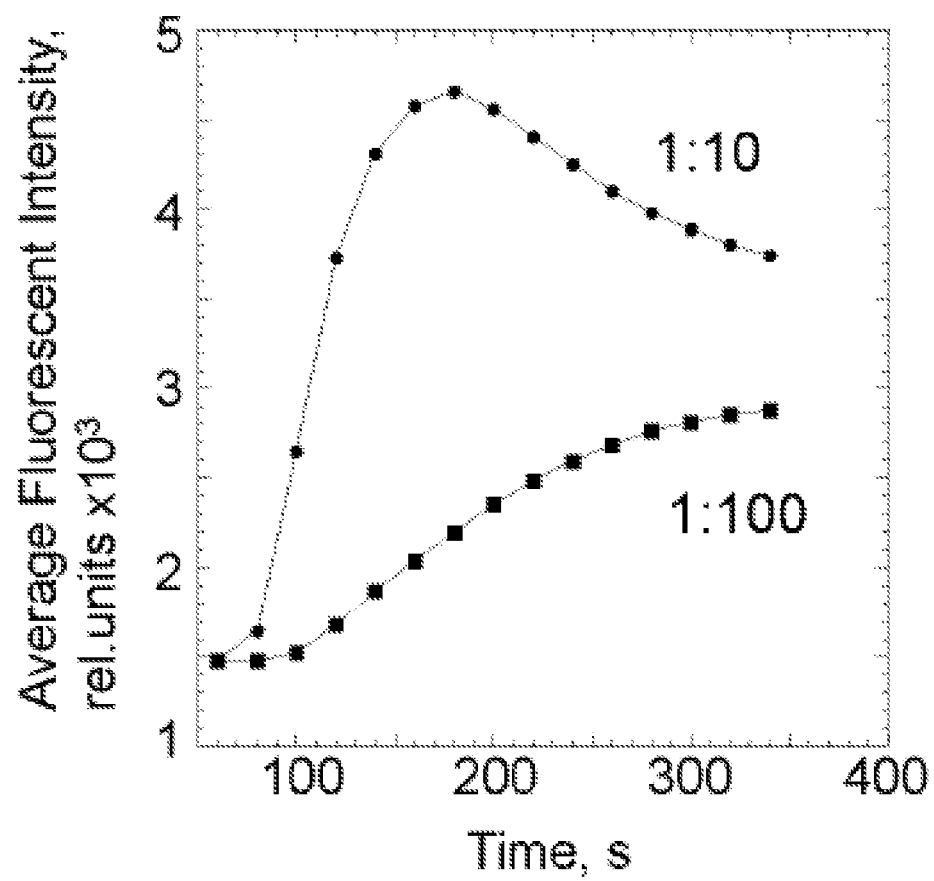
FIG. 6 depicts evaluation of $Ca^{2+}$ response by T cells after dilution of the cognate peptide with non-stimulatory peptide at different ratios.

As depicted in FIG. 5 the evaluation of the number of recognizable peptide ligands that can be detected in a monolayer of CD8 T cells in a single round of analysis. The dependence of the sensitivity of calcium response in CD8 T cells induced by a strong agonist peptide ligand diluted in a mixture of non-stimulatory peptides at indicated ratios in shown. As evident from FIG. 6, T-cell responses can be readily detected with a 10-fold excess of non-stimulatory peptides and up to 100 peptides can still be detected with a 100-fold excess of non-stimulatory peptides.

The Sensitivity of the Assay

To evaluate the sensitivity of the assay, we combined CER-43 CD8 T cells and irrelevant 115iX HLA-A2+CD8 T cells at various ratios and determined the minimal number of responsive T cells that could still be detected. In this experiment the CER-43 CTL was utilized as antigen-specific T cells, while 115iX HLA-A2+ CTL clone was used as unresponsive CD8 T cells. We combined Flu-specific CTL and non-responsive T cells at different ratios and determined a number of responsive CTL at which the cells could still be detected. The data presented in Table 2 show that as little as 3-5 responding T cells among $\sim 1 \times 10^4$ CD8 T cells per one imaging field can be reliably detected.

TABLE 2

Numbers and parameters of the responding cells per imaging field

| Cells | Field Number | Cell Area Mean +/− SD | Cell Fluorescent Intensity, Mean +/− SD | Cell Counts | Counts, Mean +/− SD |
|---|---|---|---|---|---|
| CER43:115iX 1:100 | 1 | 200 +/− 97 | 512 +/− 142 | 126 | 123 +/− 7 |
| | 2 | 200 +/− 89 | 523 +/− 156 | 115 | |
| | 3 | 208 +/− 107 | 458 +/− 147 | 128 | |
| CER43:115i 1:2000 | 1 | 158 +/− 18 | 529 +/− 127 | 5 | 4.3 +/− 1.1* |
| | 2 | 160 +/− 33 | 433 +/− 42 | 5 | |
| | 3 | 147 +/− 23 | 390 +/− 57 | 3 | |
| 115iX | 1 | 143 | 509 | 1 | 1.7 +/− 1.1* |
| | 2 | 119 | 807 | 1 | |
| | 3 | 140 +/− 22 | 483 +/− 124 | 3 | |

*P < 0.05

CER-43 is antigen specific (responding) clone

115iX is antigen non-specific (unresponding) clone

Frequency of CMV-Specific T Cells in Peripheral Blood of Normal Donors and Patients after Bone Marrow Transplantation To demonstrate usefulness of CaFlux assay in measuring the frequency of pathogen-specific T cells, we utilized frozen samples of commercially available human PBMC from healthy donors with known frequency of T cells specific for CMV-derived peptide available from C.T.L. Inc. The frequency of the CMV-specific T cells producing INF-γ was determined in ELISpot assay by the company (2295 CMV specific CD8 T cells). Table 3 shows that the frequency of the CMV-specific CD8+ T cells in healthy donors measured by CaFlux assay was about twice as large as the frequency of the T cells capable to produce INF-γ: 5,380 vs 2,295 responding CD8 T cells per $10^6$ PBMC. There are three major reasons for the observed difference. First, ELISpot assay in the provided format counts only INF-γ producing cells, while CaFlux assay detects all responding cells independently of their functionality. Second, only 50-80% of cytokine producing cells can be detected in ELISpot assay compared to 90-95% of responding cells detectable by CaFlux assay. Third, terminally differentiated, exhausted cells could die before producing enough cytokines to be measured by ELISpot.

TABLE 3

| Peptide | Field Number | Counts of CMV specific T cells per $10^4$ CD8 T cells | Mean +/− SD CMV specific T cells per $10^4$ CD8 T cells | % CD8 T cells in PBMC of the donor | Number of CMV specific T cells per $10^6$ PBMC |
|---|---|---|---|---|---|
| Cognate | 1 | 311 | 269 +/− 38 | 10% | 5,380 +/− 760 |
| | 2 | 261 | | | |
| | 3 | 235 | | | |
| Control | 1 | 4 | 7 +/− 2.6 | 10% | 140 +/− 52 |
| | 2 | 8 | | | |
| | 3 | 9 | | | |

We also examined the frequency of CMV-specific CD8+ T cells in frozen samples of PBMC derived from a patient who has undergone bone marrow transplantation. In this patient CMV reactivated on day 22nd after the transplantation. The PBMC sample was taken on 152nd day followed transplantation. For the induction of the response we utilized ProMix™ peptide pools from Thinkpeptides. The pool consists of a selected number of peptides representing the key immunodominant epitopes of human CMV with a wide range of HLA restrictions covering the most relevant HLA types in human population. The number of CD8+ T cells was 25% of initially derived PBMC as compared to 5-10% of PBMC in normal individuals. The frequency of CMV-specific CD8+ T cells was found to be and 5%, i.e., 13,825 responding CD8 T cells per $10^6$ PBMC. This is a very high frequency of the responding cells, especially taking into account that the response was induced by two peptides presented by one MHC-I allele. Thus, both parameters were significantly elevated as compared to those in samples of normal donors.

Figure 7:
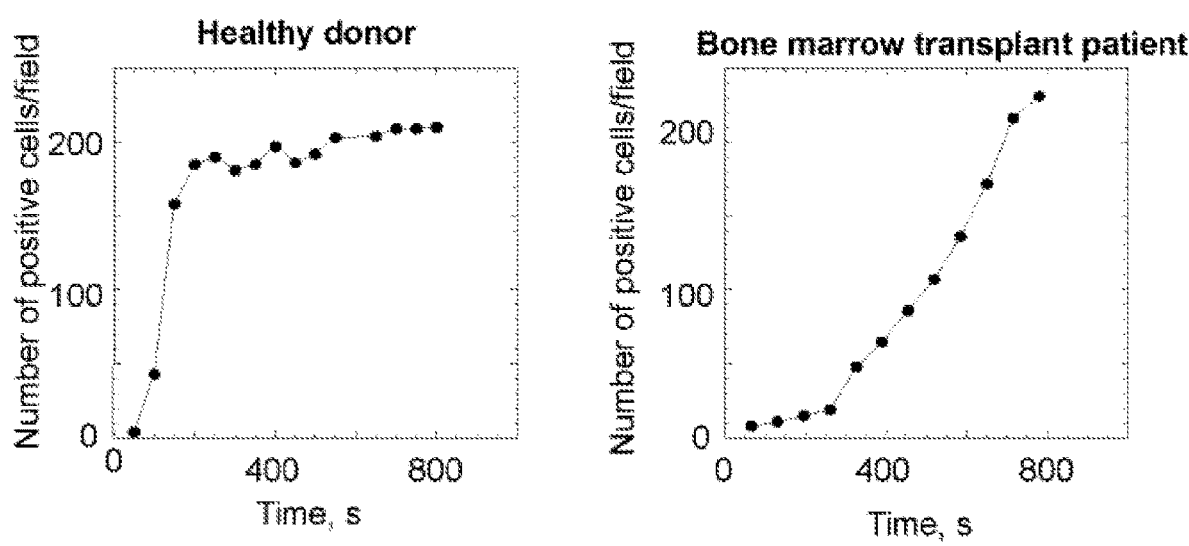
FIG. 7 depicts a graphical representation of $Ca^{2+}$ responses of T cells derived from a healthy donor and a bone marrow transplant patient by comparing the number of responding to cytomegalovirus (CMV) peptide T cells and the kinetics of the response.

As depicted in FIG. 7, kinetics of calcium response of CMV-specific memory CD8+ T cells in the glass-supported monolayers from healthy donors or patients that underwent bone marrow transplantation. Indeed, comparison of the kinetics of CMV-specific CD8 T cell responses in healthy donors and transplant patient revealed much faster response of the T cells from the donor as opposed to that from the transplant patient (FIG. 7). The response of the T cells from the patient recapitulate the response of CD8+ T cell clone towards weak agonist peptide (see FIG. 4A) suggesting that the T cells specific for the tested peptides are likely ineffective in exercising their effector functions.

Discussion

Thus far, two principal assays have been used to characterize the frequency of pathogen-specific T cells in PBMC: detection of T cells with multimeric cognate pMHC proteins (Murali-Krishna, K. et al., 1998, Immunity, 8: 177-187, Batard, P. et al., 2006, J. Immunol. Methods, 310: 136-148) and ELISpot assay, which measures production of cytokines, particularly INF-γ. Comparison of two assays with CaFlux assay is presented in Table 1. The sensitivity of CaFlux assay is very close to a lower limit of detection in the tetramer assay, i.e. 0.038%. That is similar to the limit of detection of ELISpot assay providing that the method detects few spots per 100,000 PBMC containing 2-11% of CD8 T cells.

The key advantages of the CaFlux assay is that the assay detects all T cells that are capable responding to productive TCR ligation, while tetramer assay detects only T cells whose TCR recognizes a given pMHC ligands but not necessarily respond to each ligand. ELISpot assay detects only those T cells that produce particular cytokines upon TCR stimulation. Another major difference between CaFlux Assay and ELISpot assay is the time required for completion of the analysis, i.e., few minutes vs 24-48 hours. Not only does the difference in time matter, but also the incubation of T cells for 24-48 hours in the presence of stimulatory peptides could result in activation of T cells that initially were unresponsive.

In the present study, we utilized the total fraction of CD8+ T cells. However it is evident that various subsets of CD8 T cells exercise distinct functions and could have different effect on clinical outcome (Strioga, M., et al., 2011, Immunology, 134: 17-32; Sallusto, F., et al., 1999, Nature, 401: 708-712; Lugli, E. et al., 2013, Nat. Protoc., 8: 33-42). Accordingly, in further embodiments, to analyze the subsets of the responding cells in CaFlux assay, magnetic sorting is utilized to isolate the subsets and their responses can then be measured.

In a further embodiment, alternatively, using Ibidi™ flow chambers, we could not only measure Ca2+ flux in the T cells, but could stain the cells with fluorescent-labeled antibodies for phenotype-specific markers.

In certain embodiments, it is relevant to determine the efficiency and rate of response of T cells of a patient, so as to make a determination for treatment. Accordingly, a pre-determined rate of response can be determined by calculating the rate of response to a given antigen from a set of health donor cells. An average response rate from a sufficient number of healthy cell donors can provide a baseline to the particular antigen. Upon performing the methods described herein, a patient of interest's T cells can undergo the CaFlux test to determine the rate of response of the patient's T cells and then compare the rate of response to the control. In certain embodiments, a donation set of healthy T cells can be run simultaneously to ensure a consistent control rate. The particular rate of response of the patient can inform a medical provider of potential treatment options. Where the patient's rate of response is within one standard deviation of the control, there is implication that the patient's T cells are performing efficiently, and protection against ordinary viral loads (e.g. from flu, CMV, and the like) will not likely cause problems to the patient. However, where the patient's rate of response is slower than the control by more than one standard deviation, improved viral treatments, e.g. against CMV are likely indicated to prevent increased viral loads in the patient for the particular virus of question.

This can be especially helpful in instances where certain viral loads are expected to cause problems in a particular patient. CMV is well-known for causing certain issues in certain immunocompromised patient populations, such as those undergoing chemotherapy, bone marrow transplant, radiation therapy, among others. A particular method to determine the patient's T cell response may be to perform a test of T cell response before a therapeutic process, e.g. bone marrow transplant. Wherein the response is more than one standard deviation below control, indication of an antiviral therapy is indicated.

The one-standard deviation marker can be adjusted by an ordinary physician, wherein variances of 5%, 10%, 15%, 20%, 35%, 33%, 50%, 75%, 100%, and including one, two, and three standard deviations from a control, can be utilized to determine or vary treatment. Certain protocols and viral concerns may utilize a different protocol than another, or the therapeutic treatment may differ, e.g. use of a stronger viral medication instead of a standard viral medication in certain patients. Therefore, the CaFlux provides a diagnostic mechanism to determine the rate of response of T cells and thus predicts the ability to fight off certain disease, viruses, and the like.

Accordingly, a preferred embodiment is directed to a method of determining an appropriate course of treatment, comprising performing a first CaFlux test on a patient before a pre-determined medical procedure, comparing the CaFlux test results to a control, and determining an appropriate course of treatment based on the variance from control. In certain embodiments, a CaFlux test can be performed again after the pre-determined medical procedure to compare the CaFlux results of T cells of the patient to determine whether the pre-determined medical procedure was advantageous in improving the T-cell response, or whether the pre-determined medical procedure adversely affected the patient's immune response. Appropriate therapeutic strategies can then be utilized based on the results of the before and after tests, and or either result as compared to a control.

In further embodiments the approach might be further extended to measure frequency of T cells to a set of peptides. For instance, a set of peptide epitopes from CMV eliciting a protective T-cell response are already available, and measuring the frequency of T cells recognizing these peptides is thought to be an important diagnostic and prognostic parameter.

The presented study provides a foundation for clinical application of CaFlux assay. Reliable immune monitoring of T cell responses is also essential for vaccine development and adoptive T cell transfer therapy. The frequency and quality of pathogen-specific T cells provide useful information as diagnostic, risk, prognostic and safety biomarkers and serve as a predictor of clinical outcomes during immunotherapy.

In further embodiments, the CaFlux assay also allows characterizing T cell responses in a course of autoimmune diseases including measuring of the frequency of pathogenic CD4+ T cells. Another potential application of CaFlux assay includes measuring frequency of tumor specific T cells using either tumor-associated peptides or tumor cells presenting the peptide epitopes that are layered over monolayers of T cells built in the Ibidi™ flow chambers.

For commercial applications of this approach, we propose to offer premade 96- or 384-well plates or Ibidi™ flow chambers covered with poly-L-Lysine capturing TS2/4 non-blocking mAb specific for LFA-1.

Freshly isolated T cells from healthy donors or patients whose specificity and efficiency against pathogens of cancer cells are to be tested will be labeled with $Ca^{2+}$ sensitive fluorophore and directly added to the premade plates or Ibidi™ flow chambers to form continuous monolayers.

Then peptide or a mixture of peptides that could serve as a potential antigen(s) for the tested T cells will be added to the T-cell monolayers to induce $Ca^{2+}$ response of the peptide-specific T cells. The kinetics of the $Ca^{2+}$ responses of the T cells within the monolayers will be recorded allowing determination of frequency and quality of T cells with the specificity of interest. Instead of peptides a mixture, a suspension of tumor cells could be layered over the T-cell monolayers to test the frequency and quality of tumor specific T cells.

Accordingly, a kit may comprise a premade microtiter plates or ibidi chambers will permit to produce rapidly continuous T-cell monolayers and analyze pathogen- and cancer-specific T cell responses. Combination of premade microtiter plates and available robotic technology will provide basis for high throughput assay to analyze the frequency and efficiency of pathogen- and cancer specific T cells. This will make significant contribution to establishing technologies capable to characterize responses of human immune system, one of the major goals of modern biomedical applications. The latter will allow gathering the information regarding the status on human immune system that determines in a large extent the longevity and the ability to fight pathogens and cancer.

All patents and publications cited herein are hereby fully incorporated by reference in their entirety. The citation of any publication is for its disclosure prior to the filing date and should not be construed as an admission that such publication is prior art or that the present invention is not entitled to antedate such publication by virtue of prior invention.

What is claimed is:

1. A method for detection of the frequency of T cells responding to a single or multiple antigenic peptide epitope(s), by fluorescent microscopy comprising:
   (a) coating a glass surface with an agent capable of binding an antibody, wherein the agent comprises poly-L-lysine,
   (b) immobilizing on the glass surface of (a) an antibody that binds to a receptor on the T-cell surface without interfering with $Ca^{2+}$ flux, wherein the antibody comprises the TS2/4 monoclonal antibody specific for Lymphocyte Function Associated Antigen 1 (LFA-1), to form a T-cell capturing surface,
   (c) adding cloned or polyclonal T cells or gamma/delta T cells labeled with $Ca^{2+}$ sensitive fluorophore to the T-cell capturing surface of (b) to generate a continuous monolayer of the T cells on the glass surface,
   (d) taking a first image of the T-cell monolayer to determine a level of background fluorescence in every individual cell,
   (e) performing antigen stimulation of the T-cell monolayer comprising adding a single or multiple antigenic peptide epitope(s) or live target cells presenting potential antigenic peptide epitope(s) to the T-cell monolayer wherein the antigenic peptide epitopes are capable of binding to MHC proteins expressed on the T-cell surface to form a peptide-MHC complex, (f) measuring the level of fluorescence in every individual T cell of the stimulated T-cell monolayer of (e), by taking a second image of the T-cell monolayer of (e), wherein an increase of intracellular fluorescence of individual cells indicates T cells responding to the single or multiple antigenic peptide epitopes; and g) quantifying the frequency of responses of individual T cells to a single or multiple antigenic peptide epitopes by subtracting intracellular fluorescence of the first image measured prior to addition of said single or multiple antigenic peptide(s) epitopes from that acquired after the second image following addition of said single or multiple antigenic peptide epitope(s), wherein the number of individual T cells that exhibit fluorescence greater than background fluorescence are quantified to calculate the number of responding cells per the number of added cloned or polyclonal T cells.

2. The method of claim 1, wherein the method further comprises measuring the kinetics of $Ca^{2+}$ flux in the T cells that form the monolayer on the glass surface by repeating step (f) over time to determine a kinetic curve.

3. The method of claim 1, wherein the T-cells are CD8 T cells from human peripheral blood mononuclear cells (PBMC).

* * * * *

SEQUENCE LISTING

```
<160> NUMBER OF SEQ ID NOS: 2

<210> SEQ ID NO 1
<211> LENGTH: 9
<212> TYPE: PRT
<213> ORGANISM: Artificial Sequence
<220> FEATURE:
<223> OTHER INFORMATION: IV9

<400> SEQUENCE: 1

Ile Leu Lys Glu Pro Val His Gly Val
1               5

<210> SEQ ID NO 2
<211> LENGTH: 9
<212> TYPE: PRT
<213> ORGANISM: Artificial Sequence
<220> FEATURE:
<223> OTHER INFORMATION: GL9

<400> SEQUENCE: 2

Gly Ile Leu Gly Phe Val Phe Thr Leu
1               5
```